Figure 1:
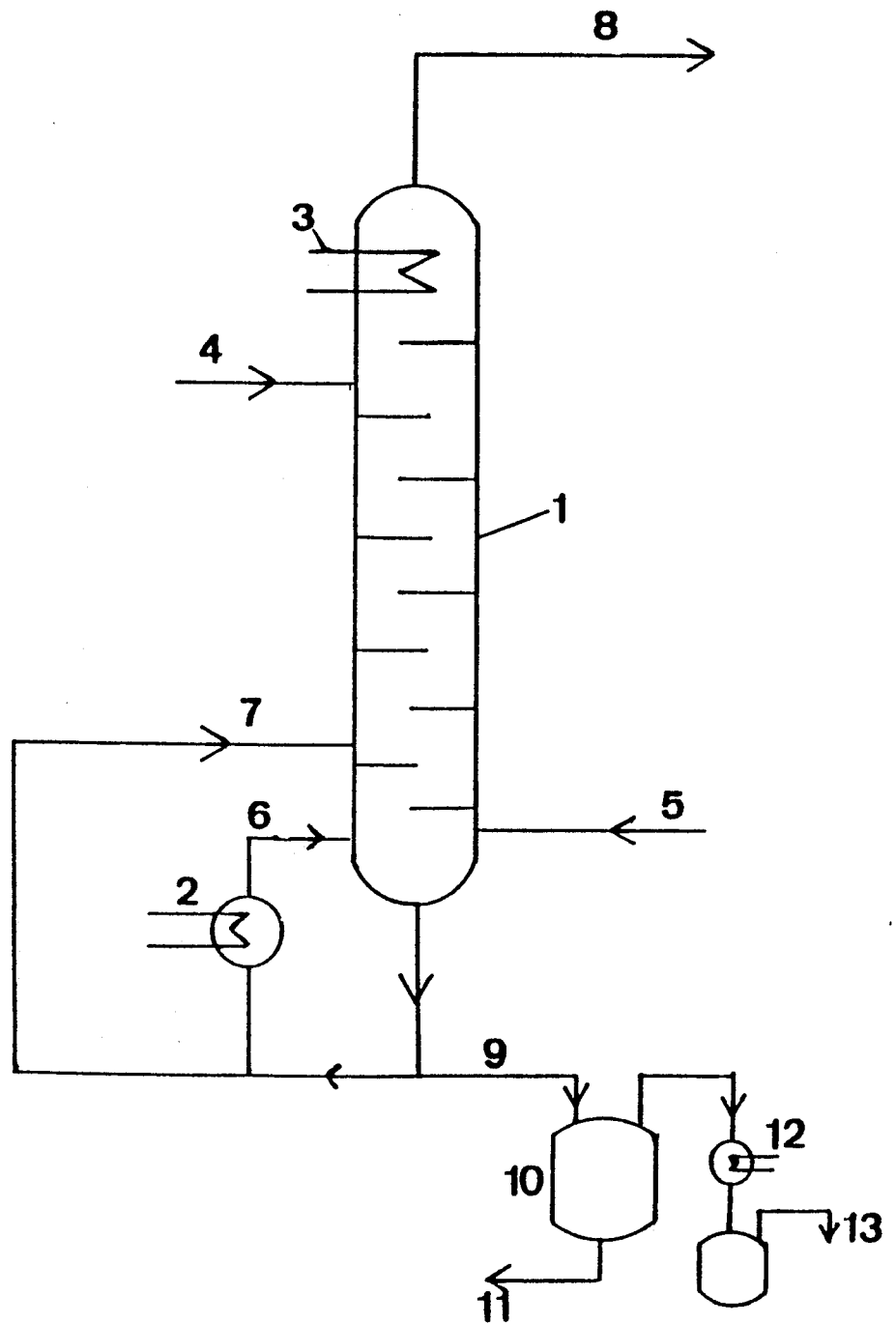

United States Patent [19]

Sajtos et al.

[11] Patent Number: 5,068,417
[45] Date of Patent: Nov. 26, 1991

[54] PROCESS FOR THE CONTINUOUS PREPARATION OF GLYOXYLIC ACID

[75] Inventors: Alexander Sajtos, Linz; Engelbert Kloimstein, Eferding; Karl Höllinger; Lorenz Farnlettner, both of Linz, all of Austria

[73] Assignee: Chemie Linz Gesellschaft m.b.H., Linz, Austria

[21] Appl. No.: 530,966

[22] Filed: May 25, 1990

[30] Foreign Application Priority Data

Jun. 5, 1989 [AT] Austria .................................. 1357/89

[51] Int. Cl.$^5$ .............................................. C07C 59/147
[52] U.S. Cl. .................................................... 562/577
[58] Field of Search ........................................ 562/577

[56] References Cited

U.S. PATENT DOCUMENTS

| | | | |
|---|---|---|---|
| 2,081,355 | 5/1937 | Heisel | 562/577 |
| 2,842,576 | 7/1958 | Habeshaw et al. | 562/577 |
| 3,014,963 | 12/1961 | Shunk et al. | 562/577 |
| 3,032,491 | 5/1962 | Barton et al. | 562/577 |
| 3,705,922 | 12/1972 | Callighan et al. | |
| 4,026,929 | 5/1977 | Bauer et al. | 562/577 |
| 4,340,748 | 7/1982 | Baltes et al. | 562/577 |
| 4,867,849 | 7/1989 | Cova et al. | 562/577 |

FOREIGN PATENT DOCUMENTS

| | | |
|---|---|---|
| 376197 | 10/1984 | Austria . |
| 0099981 | 1/1986 | European Pat. Off. . |
| 0293127 | 11/1988 | European Pat. Off. . |

Primary Examiner—Bruce Gray
Attorney, Agent, or Firm—Wenderoth, Lind & Ponack

[57] ABSTRACT

A process for continuous preparation of a concentrated aqueous solution of glyoxylic acid by hydrolysis of glyoxylic acid ester hemiacetals, wherein glyoxylic acid ester hemiacetals are treated with steam in countercurrent in a reactor cascade.

9 Claims, 1 Drawing Sheet

PROCESS FOR THE CONTINUOUS PREPARATION OF GLYOXYLIC ACID

The invention relates to a process for the continuous preparation of a pure concentrated aqueous solution of glyoxylic acid having a low color number by hydrolysis of alkyl glyoxylate hemiacetals.

Glyoxylic acid in the form of an approximately 50% solution is a valuable starting product for the manufacture of plant protection agents, medicaments, fragrances and aroma substances as well as plastics intermediates. Particularly in the use for the manufacture of medicaments, fragrances and aroma substances as well as plastics intermediates, stringent demands on the purity, color and stability of the glyoxylic acid solution must be met.

EP-B 0,099,981 describes the preparation of glyoxylic acid by ozonolysis of dialkyl maleates in alcoholic solution, catalytic reduction of the resulting peroxide to the hemiacetal and subsequent hydrolysis by heating with water. The disadvantage here is that the dialkyl oxalate, arising as a by-product in the preparation of the hemiacetal, is hydrolysed to oxalic acid and about 2-5% of oxalic acid remain in the glyoxylic acid as a by-product which interferes with further processing. The alcohol/water mixture formed in the hydrolysis is distilled out of the reaction mixture, which involves a relatively high thermal stress on the glyoxylic acid and relatively long reaction times if the alcohol is completely separated off. This stress on the thermally unstable glyoxylic acid leads to the formation of by-products, some of which are insoluble and some of which are deeply colored and which can no longer be completely separated off, so that the higher color number results in restrictions regarding the use of glyoxylic acid prepared in this way. Although it is possible to accelerate the hydrolysis of the hemiacetal by an addition of mineral acid, whereby the reaction time is shortened, traces of acid remain in the end product as impurities which cannot be separated off.

Surprisingly, a process for the preparation of a pure concentrated aqueous solution of glyoxylic acid having a low color number by hydrolysis of glyoxylic acid ester hemiacetals has now been found, wherein an approximately 50% glyoxylic acid solution of high purity, low color number and good color stability is obtained in a good yield under mild conditions.

Accordingly, the invention relates to a process for the continuous preparation of a pure concentrated aqueous solution of glyoxylic acid having a low color number by hydrolysis of glyoxylic acid ester hemiacetals, which is characterized in that glyoxylic acid ester hemiacetals are treated with steam in countercurrent in a reactor cascade.

The starting compounds, namely the glyoxylic acid ester hemiacetals, can be prepared according to EP-B 0,099,981 which has already been mentioned. Preferably, those glyoxylic acid ester hemiacetals are used which, on hydrolysis, release an alcohol whose boiling point, or whose boiling point in the azeotrope with water, is below 100° C. Examples of such glyoxylic acid ester hemiacetals are methyl glyoxylate methyl-hemiacetal, ethyl glyoxylate hemiacetals, propyl glyoxylate hemiacetals, i-propyl glyoxylate hemiacetals, t-butyl glyoxylate hemiacetals and n-butyl glyoxylate hemiacetals. With particular preference, methyl glyoxylate methyl-hemiacetal is used.

For carrying out the reaction, the alkyl glyoxylate hemiacetal is, if appropriate in solution with an aliphatic alcohol having 1 to 4 C atoms, fed to the upper part of the reaction cascade and treated in counter-current with steam, the mass ratio of alkyl glyoxylate hemiacetal to steam being at least 1:1 to 1.5 and preferably 1:1.2 to 1.35, in order to ensure also the hydrolysis of acetals which may be present.

The reactor cascade is preferably in the form of a tray column, it being advantageous to use a column having a defined quantity of liquid on the trays (hold-up), which is intended to avoid the trays running dry.

The residence time in the reactor cascade should allow as quantitative as possible a hydrolysis of the alkyl glyoxylate hemiaceta.,1 but should also be as short as possible in order to minimize the thermal stress on the glyoxylic acid. The residence time necessary to achieve this depends on the quantity of liquid on the trays and on the number of trays in the reactor cascade. As a rule, residence times of 30-60 minutes are sufficient.

The top temperature of the reactor cascade is controlled in such a way that the alcohol formed in the hydrolysis is stripped out of the column together with the excess steam. The bottom temperature of the column is controlled in such a way that an approximately 44-46% solution of glyoxylic acid is obtained at the bottom of the column. As a rule, the bottom temperature is about 110°-125° C. and the top temperature is about 90°-100° C., a temperature difference of at least 20° C. being maintained preferably.

Within the entire range, the temperature at the top of the column is controlled in such a way that sufficient reflux is ensured. Simultaneously with the alcohol/water mixture leaving over the top, any higher-boiling by-products which may be present in the starting product and are difficult to hydrolyze and are volatile with steam, such as dialkyl oxalates, are also stripped out, which results in additional purification The oxalic acid content in the end product is thereby reduced to about 0.5%.

An about 44-46% glyoxylic acid solution is taken off from the bottom of the column and then let down into an evacuated vessel, the solution being concentrated to at least 50%, simultaneously and in addition to the rapid cooling. The water vapor released is condensed and taken off.

Advantageously, a part of the glyoxylic acid solution taken off at the bottom is recycled into the lower third of the column, the hydrolysis of the remaining glyoxylic acid hemiacetal being catalytically accelerated by the increased glyoxylic acid concentration in the lower part of the column As a result, the alcohol content in the free or bound form in the bottom product is reduced to less than 1 g/l of 50% glyoxylic acid solution.

FIG. 1 shows a preferred embodiment of the process according to the invention. In FIG. 1, 1 marks a reactor cascade, preferably a bubble-cap tray column, 2 marks a heater, 3 marks a dephlegmator, 4 marks a feed line for the alkyl glyoxylate hemiacetal, 5 marks a steam feed line, 6 marks a feed line for the vapors from the heater 2, 7 marks a glyoxylic acid feed line for the recycle, 8 marks a vapor pipe, 9 marks a take-off line for the glyoxylic acid solution, 10 marks a receiver tank, 11 marks a take-off line for the cooled and concentrated glyoxylic acid solution, 12 marks a condenser and 13 marks a vacuum line.

Alkyl glyoxylate hemiacetal, if appropriate in alcoholic solution, is fed into the column via line 4 at a temperature of about 20–100° C. Superheated steam is fed via line 5 and passed upwards through the column.

At the bottom of the column, a part of the glyoxylic acid solution formed is taken off and heated by means of a heater 2, and the vapors are returned into the column via line 6. A part of the glyoxylic acid taken off at the bottom is recycled via line 7 into the lower third of the column. An approximately 44–46% glyoxylic acid solution is taken off via line 9 at a temperature of 110°–125° C., let down into an evacuated receiver tank 10 at about 50 mbar and cooled, the escaping water vapor being condensed in the condenser 12. At the top of the column, the temperature is controlled by a dephlegmator 3 in such a way that the alcohol/water mixture, as well as any higher-boiling by-products which may be present and are difficult to hydrolyze and are volatile with steam, escape through the vapor pipe 8.

According to the process described, glyoxylic acid is obtained in high purity in yields of 95–98%, relative to the starting product The mean residence time is in general only between 30 and 60 minutes, whereby the formation of by-products which are insoluble or cannot be separated off and impair the purity and color of the glyoxylic acid, is avoided.

The glyoxylic acid prepared according to the invention shows a Gardener color number (ASTM D 1544-8) of 1 to 2, and this does not deteriorate even on prolonged storage.

EXAMPLE 1

In an experimental apparatus according to FIG. 1, consisting of a bubble-cap tray column having 27 trays and a diameter of 300 mm, 85 kg of methyl glyoxylate hemiacetal per hour were fed at point 4 to the 21st tray and 115 kg of steam under an upstream pressure of 7 bar were fed at point 5. At the same time, about 30 kg of hot bottom product were recycled to point 7 on the 7th tray. The heat exchanger 2 was heated with 3.3 bar steam. A bottom temperature of 114°–115° C. was established. The top temperature below the dephlegmator was between 96 and 98° C. Under these conditions, 113 kg of glyoxylic acid solution per hour were discharged as bottom product from the column into the tank 10. As a result of the vacuum evaporation at about 65 mbar, 10–12 1 of water per hour were also vaporized and about 100 kg of virtually colorless 51 to 52% glyoxylic acid solution were obtained. The product contained less than 1 g of methanol/kg. At a total column hold-up of 60 1, this gave an average residence time of the glyoxylic acid in the reaction system of 40 to 45 minutes.

The glyoxylic acid solution obtained showed a Gardener color number of 1–2 and had the following composition:

| Glyoxylic acid | 51.9% |
| --- | --- |
| Glyoxal | not detectable |
| Oxalic acid | 0.5% |
| Succinic acid | not detectable |
| Maleic acid | no longer detectable |
| Methanol | 70 ppm |
| Formic acid | not detectable |

Comparison example 500 kg of methyl glyoxylate hemiacetal and 600 kg of water were introduced into a 1500 1 reaction vessel with stirrer, steam heating and a 3 m long packed column and condenser with reflux divider, and heated to the boil with stirring. As soon as boiling under reflux started, distillate take-off was begun. At a top temperature of about 75° C., more than 90% of the methanol eliminated was distilled off in the course of 5 hours. The top temperature was then increased up to 97° C., the methanol decreasing to less than 5 g/kg of reaction solution in the course of a further 3 hours. At a boiling temperature of 108-110° C., 616 kg of 50% glyoxylic acid solution having a light brown color were obtained. In addition, 484 kg of methanol/water mixture were obtained as the distillate, from which methanol can be recovered.

The glyoxylic acid prepared in this way showed a Gardener color number of 7–8 and was unsuitable for use as the starting compound for the manufacture of pharmaceuticals, fragrances and aroma substances as well as plastics intermediates.

| Composition: | |
| --- | --- |
| Glyoxylic acid | 50% |
| Glyoxal | not detectable |
| Oxalic acid | 4% |
| Succinic acid | not detectable |
| Maleic acid | not detectable |
| Methanol | 5 g/kg |
| Formic acid | not detectable |

What we claim is:

1. Process for the continuous preparation of a pure concentrated aqueous solution of glyoxylic acid having a low color number by hydrolysis of glyoxylic acid ester hemiacetals, comprising treating the glyoxylic acid ester hemiacetals with steam in countercurrent in a reactor cascade.

2. Process according to claim 1, comprising using glyoxylic acid ester hemiacetals which, on hydrolysis, release alcohols whose boiling point, or whose boiling point in the axeotrope with water, is below 100° C.

3. Process according to claim 2, comprising using methyl glyoxylate methyl-hemiacetal.

4. Process according to claim 1, comprising the glyoxylic acid ester hemiacetal: steam mass ratio being 1:1.2 to 1.35.

5. Process according to claim 1, comprising the residence time in the reactor cascade being 30–60 minutes.

6. Process according to claim 1, comprising taking off a part of the glyoxylic acid solution at the lowest tray of the cascade and recycling it into the reactor cascade.

7. Process according to claim 1, comprising concentrating the glyoxylic acid solution taken off at the lowest tray in vacuo.

8. Process according to claim 1, comprising maintaining a temperature of 110°–125° C. in the bottom of the reactor cascade and a temperature of 90°–100° C. at the top of the reactor cascade.

9. Process according to claim 1, comprising maintaining a temperature difference of at least 20° C. between the bottom and top of the reactor cascade.

UNITED STATES PATENT AND TRADEMARK OFFICE
CERTIFICATE OF CORRECTION

PATENT NO. : 5,068,417
DATED : November 26, 1991
INVENTOR(S) : Alexander SAJTOS et al.

It is certified that error appears in the above-identified patent and that said Letters Patent is hereby corrected as shown below:

On the title page, in item (75):

Change the last name of the fourth inventor from "Farnlettner" to --Farnleitner--.

Signed and Sealed this

Sixth Day of July, 1993

*Attest:*

MICHAEL K. KIRK

*Attesting Officer*      Acting Commissioner of Patents and Trademarks